(12) United States Patent
Boehm

(10) Patent No.: US 8,453,887 B2
(45) Date of Patent: Jun. 4, 2013

(54) ONE-PIECE VENTED PISTON

(75) Inventor: Andreas J. Boehm, Reichling (DE)

(73) Assignee: 3M Innovative Properties Company, Saint Paul, MN (US)

( * ) Notice: Subject to any disclaimer, the term of this patent is extended or adjusted under 35 U.S.C. 154(b) by 219 days.

(21) Appl. No.: 12/594,290

(22) PCT Filed: Nov. 6, 2008

(86) PCT No.: PCT/US2008/082582
§ 371 (c)(1),
(2), (4) Date: Oct. 1, 2009

(87) PCT Pub. No.: WO2009/061884
PCT Pub. Date: May 14, 2009

(65) Prior Publication Data
US 2010/0294795 A1 Nov. 25, 2010

(30) Foreign Application Priority Data
Nov. 7, 2007 (GB) .................................. 0721774.8

(51) Int. Cl.
*B67D 7/60* (2010.01)
*G01F 11/00* (2006.01)
(52) U.S. Cl.
USPC .............. 222/387; 222/386; 222/326; 433/90
(58) Field of Classification Search
USPC ...... 222/326, 386–387; 604/122, 218; 433/90
See application file for complete search history.

(56) References Cited

U.S. PATENT DOCUMENTS

| 385,477 A | 7/1888 | Pitney |
|---|---|---|
| 3,998,224 A | 12/1976 | Chiquiar-Arias |
| 4,252,118 A | 2/1981 | Richard et al. |
| 4,572,210 A | 2/1986 | Mckinnon |
| 4,632,672 A | 12/1986 | Kvitrud |
| 4,660,569 A | 4/1987 | Etherington |
| 4,792,065 A | 12/1988 | Soehnlein et al. |
| 4,826,483 A | 5/1989 | Molnar, IV |
| 4,852,772 A | 8/1989 | Ennis, III |

(Continued)

FOREIGN PATENT DOCUMENTS

| EP | 0 900 599 | 3/1999 |
|---|---|---|
| EP | 1 738 834 | 1/2007 |

(Continued)

OTHER PUBLICATIONS

International Search Report for PCT/US2008/082582.

*Primary Examiner* — Kevin P Shaver
*Assistant Examiner* — Nicholas J Weiss
(74) *Attorney, Agent, or Firm* — Carlos M. Téllez; 3M Innovative Properties Company

(57) ABSTRACT

A vented piston (1) comprises a plunger (2) having a front side and a rear side, a venting passage (4) extending between the front side and the rear side, and a cap (7) located adjacent the front side. The cap is resiliently-biased by a spring (8) towards an open position in which air can pass through the venting passage from the front to the rear side of the plunger, and is movable from the open position into a closed position in which the cap closes the venting passage. The piston may be used in a storage chamber (10) of a dispensing system whereby air can be removed from the storage chamber by moving the plunger in the direction of a substance (12) stored in the chamber.

19 Claims, 6 Drawing Sheets

U.S. PATENT DOCUMENTS

| | | | |
|---|---|---|---|
| 5,021,047 A | 6/1991 | Movern | |
| 5,042,695 A | 8/1991 | Battegazzore | |
| 5,178,305 A | 1/1993 | Keller | |
| 5,183,466 A | 2/1993 | Movern | |
| 5,316,186 A * | 5/1994 | Prestele | 222/327 |
| 5,453,093 A | 9/1995 | Haining | |
| 5,626,887 A * | 5/1997 | Chou et al. | 425/129.1 |
| 5,738,655 A | 4/1998 | Vallelunga et al. | |
| 5,865,803 A | 2/1999 | Major | |
| 5,874,354 A | 2/1999 | Heitzer et al. | |
| 5,878,922 A * | 3/1999 | Boring | 222/387 |
| 6,095,814 A | 8/2000 | Petrich et al. | |
| 6,572,565 B2 | 6/2003 | Daley et al. | |
| 6,598,766 B1 | 7/2003 | Brugner | |
| 6,632,198 B2 | 10/2003 | Caizza | |
| 6,685,063 B2 * | 2/2004 | Brugner | 222/387 |
| 6,843,652 B2 * | 1/2005 | Xie et al. | 433/90 |
| 6,899,254 B1 * | 5/2005 | Sandholm et al. | 222/387 |
| 6,916,308 B2 | 7/2005 | Dixon et al. | |
| 7,101,351 B2 | 9/2006 | Crawford et al. | |
| D581,528 S | 11/2008 | Sudo | |
| D583,938 S | 12/2008 | Sudo | |
| 7,503,905 B2 | 3/2009 | Jessop et al. | |
| 7,547,297 B2 | 6/2009 | Brinkhues | |
| 7,654,418 B2 * | 2/2010 | Law et al. | 222/259 |
| 7,748,577 B2 * | 7/2010 | Brugner | 222/387 |
| 2002/0076671 A1 | 6/2002 | Markus et al. | |
| 2002/0077598 A1 | 6/2002 | Yap et al. | |
| 2003/0120220 A1 | 6/2003 | Lee et al. | |
| 2003/0196914 A1 | 10/2003 | Tzou et al. | |
| 2003/0233075 A1 | 12/2003 | Huegli | |
| 2005/0006809 A1 | 1/2005 | Stroppiana | |
| 2005/0137533 A1 | 6/2005 | Sudo et al. | |
| 2006/0178643 A1 | 8/2006 | Sudo et al. | |
| 2007/0078406 A1 | 4/2007 | Lee | |
| 2007/0078407 A1 | 4/2007 | Huang | |
| 2007/0167910 A1 | 7/2007 | Tennican | |
| 2007/0172789 A1 | 7/2007 | Muller et al. | |
| 2007/0250004 A1 | 10/2007 | Tung | |
| 2008/0097387 A1 | 4/2008 | Spector | |
| 2010/0200617 A1 | 8/2010 | Schär | |

FOREIGN PATENT DOCUMENTS

| | | |
|---|---|---|
| EP | 2 221 257 | 8/2010 |
| GB | 1 475 430 | 6/1977 |
| JP | 4-200672 | 7/1992 |
| WO | WO 97/12394 | 4/1997 |
| WO | WO 01/94028 | 12/2001 |
| WO | WO 2005/016783 | 2/2005 |
| WO | WO 2007/047381 | 4/2007 |
| WO | WO 2007/104037 | 9/2007 |
| WO | WO 2008/005654 | 1/2008 |
| WO | WO 2009/029974 | 3/2009 |

* cited by examiner

ONE-PIECE VENTED PISTON

CROSS-REFERENCE TO RELATED APPLICATIONS

This application is a national stage filing under 35 U.S.C. 371 of PCT/US2008/082582, filed Nov. 6, 2008, which claims priority to United Kingdom Patent Application No. 0721774.8 filed Nov. 7, 2007, the disclosure of which is incorporated by reference herein.

FIELD OF THE INVENTION

The present invention relates to pistons of the type that enable air to be vented from a chamber in which the piston is located.

BACKGROUND OF THE INVENTION

The invention is concerned, more especially, with pistons suitable for use in dispensing systems that also function to store a substance to be dispensed until it is required for use. Dispensing systems of that type are known, for example, in the field of dentistry where dental materials such as impression materials, restoration materials and filler materials are often supplied in cartridges comprising a storage chamber in which the material, or a component thereof, is contained. Such a cartridge may be provided, at its front end, with a sealed dispensing outlet and, at its rear end, with a piston that closes the storage chamber. When the dental material is required, the dispensing outlet is opened and the piston is driven into the storage chamber to dispense the contents through the outlet. The dental material may consist of one component only, or of two or more components that are to be mixed together for use: in the latter case, the components may be contained in separate storage chambers within the cartridge. Increasingly, in the dental field, single-use cartridges are employed with hand-held applicators that enable a dental practitioner to dispense a dental material from the cartridge directly to a selected site within a patient's mouth.

Dispensing cartridges suitable for dental materials are described, for example, in WO 2005/016783 and WO 2007/047381.

A problem that is frequently encountered when filling a substance into a dispensing system in which it is intended to be stored is that of removing air from the storage chamber and ensuring that no voids or air bubbles are trapped in the stored substance. The presence of air may have an adverse effect on the shelf life of the stored substance, and the presence of voids or air bubbles may have an adverse effect on the accuracy with which metered quantities of the substance can be dispensed. One conventional way of addressing this problem is to assemble the dispensing system under vacuum but this can result in the evaporation of ingredients from the substance to be stored and a consequent alteration in its composition. Another way of addressing the problem is to fill the system through its dispensing outlet but this method can only be used with systems that are appropriately configured.

It has also been proposed to address the problem by using a so-called vented piston in the storage chamber of the dispensing system. Storage and dispensing systems that incorporate some form of vented piston are described, for example, in U.S. Pat. No. 4,632,672; U.S. Pat. No. 5,178,305 and U.S. Pat. No. 6,899,254 and in WO 01/94028, as well as the above-mentioned WO 2005/016783 and WO 2007/047381.

SUMMARY OF THE INVENTION

The present invention is concerned with the provision of a vented piston assembly, suitable for use in storage and dispensing systems, which is of comparatively simple construction but capable of ensuring the effective removal of air from a substance that is being stored within the system.

The present invention provides a vented piston comprising a plunger having a front side and a rear side, a venting passage extending between the front side and the rear side, and a cap located adjacent the front side; wherein the cap is resiliently-biased towards an open position in which air can pass through the venting passage from the front to the rear side of the plunger, and is movable from the open position to a closed position in which the cap closes the venting passage.

When used in a storage chamber of a dispensing system, a piston in accordance with the invention can be used to allow air to escape from within the chamber as the plunger is inserted. The air-removal process terminates when the cap moves into the closed position, which may occur, for example, when the plunger has contacted a substance in the storage chamber and the cap moves into the closed position under the resulting pressure on the front side of the plunger. The closed position of the cap may then be maintained, for example by continued pressure on the front side of the plunger or because the cap is a tight fit in the venting passage. The plunger may be provided, at its periphery, with sealing means that engages the wall of the storage chamber to seal the front side of the plunger from the rear side. The sealing means may also function to maintain the position of the plunger in the storage chamber following movement of the cap into the closed position. In a dispensing system of that type, the substance may be loaded into the storage chamber before the piston is inserted. This may facilitate access to the storage chamber and enable filling times to be optimized.

Pistons in accordance with the invention can be formed with comparatively small dimensions that make them suitable for use in dispensing cartridges for dental materials, especially cartridges that are intended to dispense dental materials directly into a patient's mouth. A cartridge of the latter type may, for example, employ a piston having a diameter of about 4.0 mm, and piston diameters in the range of from 4.0 to 6.0 mm or, more generally, 3.0 to 10.0 mm are typical in this field.

Suitable materials for pistons in accordance with the invention (particularly, but not exclusively, for use in the dental field) are polypropylene (PP), polyethylene (PE), acrylonitrile butadiene styrene (ABS), polyoxymethylene (POM), polycarbonate (PC), polystyrene (PS), polybutylene terephthalate (PBT), acrylonitrile butadiene styrene (ABS), polyoxymethylene (POM), and/or polyamide (PA).

In a piston in accordance with the invention, the cap may be resiliently biased towards the open position by a spring. Advantageously, the spring is formed as a one-piece moulded component together with the cap and at least a part of the plunger. This enables the piston to be manufactured in a comparatively simple and cost-effective manner.

In an embodiment of the invention, the spring extends at least partially around the cap. The length of the spring may thereby be substantially greater than the distance traveled by the cap in moving between the open and closed positions. This may be of advantage particularly in a piston of comparatively small dimensions such as those used in dental cartridges in that it can enable the cap to respond to comparatively low forces, and to respond readily to changes in pressure exerted on its front side. It can also assist, when the piston is used in the storage chamber of a dispensing system, in ensuring that the cap remains in the closed position while a substance is being stored in the chamber following the removal of air therefrom.

The plunger of the piston assembly is advantageously hollow, providing a buffer space that can be used, if required, to compensate for variable filling of a storage system in which the piston assembly is employed. This may be of utility in the particular case of dental cartridges that are filled by an automated process, when the small size of the storage chambers within the cartridges (typically in the range of from 100 to 500 mm$^3$) may give rise to comparatively high filling tolerances (in the range, for example, of from 10 to 20%). A hollow piston also offers access for a setting tool, inserted into the plunger from the rear side thereof to engage the cap and control its movement into the closed position. The setting tool may, for example, be used to hold the cap in the open position, or to pull it into the closed position.

In a method of storing a substance in a storage chamber using a piston in accordance with the invention, the substance is advantageously be loaded into the chamber before the piston is inserted in the chamber. The piston is then moved into the chamber to bring the plunger into contact with the substance, thereby removing air from the chamber through the venting passage. In a method suitable for being automated, the cap is held open and is only allowed to move into the closed position when the piston is has moved into the chamber by a distance sufficient to bring the plunger into contact with the minimum amount of the substance that is likely to be present in the chamber.

BRIEF DESCRIPTION OF THE DRAWINGS

By way of example only, embodiments of the invention will now be described with reference to the accompanying drawings, in which.

DETAILED DESCRIPTION

Figure 1:
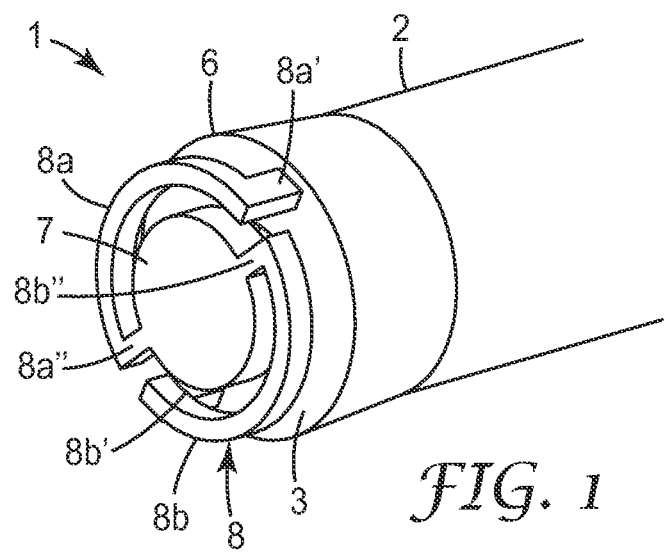
FIG. 1 is a perspective view of the front end of a piston in accordance with the invention.
Figure 2:
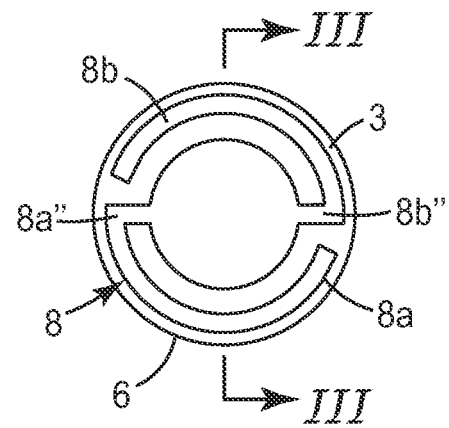
FIG. 2 is a front end view of the piston.
Figure 3:
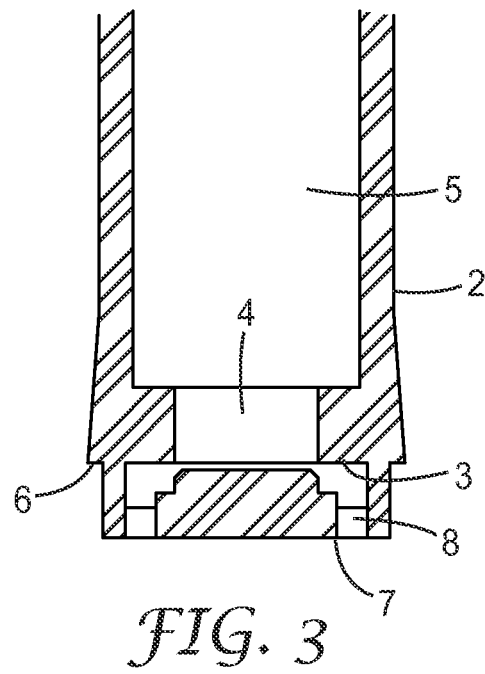
FIG. 3 is a longitudinal cross-section of the front end of the piston, on the line III-III in FIG. 2.

FIGS. 1 to 3 show a vented piston 1 suitable for use in a storage chamber of a dispensing cartridge (not shown) that will be described below. The assembly 1 comprises a hollow plunger 2 having a front end wall 3 through which extends a venting passage 4 providing a connection between the front side and the rear side of the plunger. The interior of the plunger 2 forms a passageway 5, which extends from the front end of the plunger to its rear end (not shown). Externally, the plunger 2 is flared outwards slightly at its front end to form a sealing lip 6, the purpose of which will be described below.

The piston 1 further comprises a cap 7 positioned adjacent the front side of the front end wall 3 of the plunger 2 and connected to the front end wall by a spring 8 (described in greater detail below). The cap 7 is shaped to seat on the front end wall 3 and close the venting passage 4, but is resiliently-biased by the spring 8 into the open position shown in FIGS. 1 to 3, in which there is a slight gap between the cap and the plunger 2.

In one exemplary use, the piston 1 is inserted into a storage chamber 10 of a dispensing cartridge 11 (partly shown in FIG. 4) with the front side of the front end wall 3 facing towards a substance 12 that has been loaded into the cartridge for storage and subsequent use. In this case, the cartridge 11 has a dispensing outlet at its front end (not shown) through which the substance 12 can be dispensed by pushing the plunger 2 of the piston into the storage chamber 10. Except at the sealing lip 6, the outer diameter of the plunger 2 is such that there is a clearance 13 between the plunger and the wall of the storage chamber 10. The lip 6, on the other hand, seals against the wall of the storage chamber 10 and prevents communication between the front and rear sides of the plunger around the outside of the latter. Any other appropriate mechanism for preventing communication between the front and rear sides of the plunger could be used.

Figure 4:
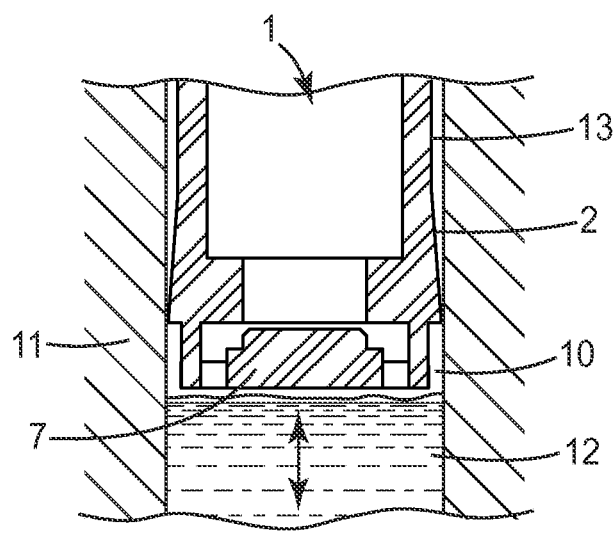
FIG. 4 shows the piston as in FIG. 3, in the storage chamber of a dispensing cartridge.
Figure 5:
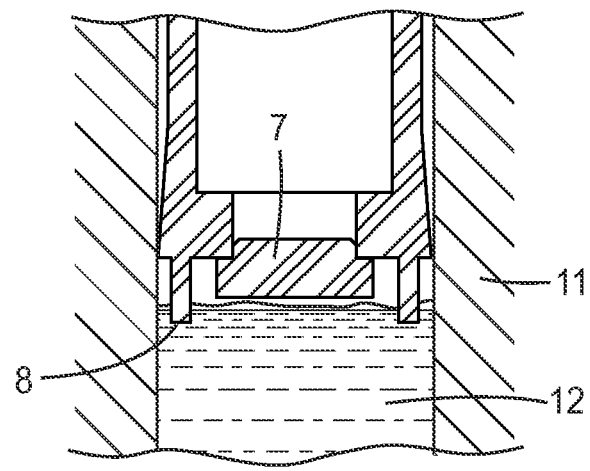
FIG. 5 is a similar view to FIG. 4 but shows the cap of the piston in a closed position.

FIG. 4 shows a stage in the process of removing air from the storage chamber 10 to increase the length of time for which the substance 12 can be stored in a good condition. Prior to this stage, and before the piston 1 was inserted into the chamber 10, the substance 12 was loaded into the chamber from the rear end of the latter. In the situation shown in FIG. 4, the piston assembly 1 has been inserted into the chamber 10 but the plunger 2 has not yet been pushed far enough into the chamber to contact the substance 12. The cap 7 is in the open position and, as the plunger 2 is moved into the chamber, it is possible for air to flow from the front to the rear side of the plunger by passing around the cap 7 and through the venting passage 4, and then to escape through the passageway 5 in the plunger 2. The air removal process is completed by pushing the plunger 2 further into the storage chamber 10 until it contacts the substance 12. A small amount of the substance 12 will then flow into the venting passage 4 but the pressure exerted by the substance 12 of the front face of the cap 7 will quickly overcome the biasing force of the spring 8 and move the cap into the closed position shown in FIG. 5 in which it blocks the venting passage 4. The substance 12 is now enclosed within the storage chamber 10 in a substantially air-free condition as a result of the air having been removed through the venting passage as the piston 1 was being inserted into the cartridge 11. The fact that the piston 1 has reached this storage position could, if required, be detected by an increase in the pressure required to move the piston further into the storage chamber 1, indicating that the cap 7 has moved into the closed position. The piston 1 then remains in the storage position shown in FIG. 5, being held by the sealing engagement of the lip 6 with the wall of the storage chamber, until the cartridge is required for use.

It will be appreciated that the above-described process for filling the cartridge 11 and removing air from the stored substance 12 is one that would typically be automated. From that perspective, the fact that the substance 12 is loaded into the chamber 10 from the rear end of the cartridge before the piston 1 is inserted is advantageous because access to the chamber 10 is unimpeded, and the filling process can be carried out efficiently.

Figure 6:
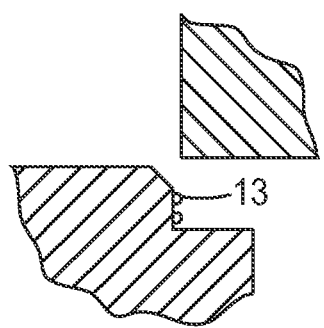
FIG. 6 illustrates a modification of part of the piston of FIGS. 1 to 3.

When the cartridge 11 is required for use, the dispensing outlet of the cartridge is opened and a force is applied to the rear of the plunger 2 to overcome the holding force of the sealing lip 6 and drive the plunger further into the storage chamber 10, thereby forcing the substance 12 out of the chamber through the dispensing outlet. The plunger 2 may be driven into the chamber 10 by manual pressure applied directly to the rear of the plunger. Alternatively, the cartridge may be inserted into a suitable applicator provided for this purpose. As the plunger 2 moves into the chamber 10, the pressure on the front face of the cap 7 increases so that it remains even more firmly seated on the plunger 2 thereby reducing the risk of the stored substance 12 passing into the venting passage 4. If required, however, one or more sealing rings 13 or other suitable sealing features can be provided on the cap 7 (see FIG. 6) and/or the adjacent surface of the plunger 2 to ensure that the venting passage 4 is completely blocked when the cap 7 is in the closed position.

The construction of the plunger 2 of the piston 1, and especially the front end thereof, will now be described in greater detail. The plunger 2, cap 7 and spring 8 are injection-moulded in one piece from a suitable plastic material, for example polypropylene, polyoxymethylene or polybenzothiazole. For the purposes of the injection-moulding process, the spring 8 comprises two parts 8a, 8b, each of which encircles a respective half (approximately) of the cap 7. Each spring part 8a, 8b is connected at one end to the plunger 2 by a respective post 8a', 8b', that stands up from the front end face of the plunger and spaces the spring part from that end face. At the other end, each spring part 8a, 8b is connected to the cap 7 by a respective inwardly-extending arm 8a'', 8b''. The spring parts 8a, 8b and the connecting posts and arms 8a', 8b', 8a'', 8b'' are moulded so that, in its normal position, the spring 8 holds the cap 7 in the open position. The spring is contained within the perimeter of the front end face of the plunger 2 (i.e. within the lateral dimensions of the plunger) and is also contained within the travel of the cap between its open and closed positions: consequently, no additional space is required to accommodate the spring. In addition, the length of the spring parts 8a, 8b is substantially greater than the distance traveled by the cap 7 in moving between its open and closed positions so that the cap responds readily to changes in pressure on its front face due to the presence of a substance 12 in the storage chamber 10. In particular, a comparatively small increase in pressure on the front face of the cap 7 will be sufficient to move the cap into the closed position, which assists in ensuring that the cap remains in the closed position in the situation illustrated in FIG. 5.

Figure 7:
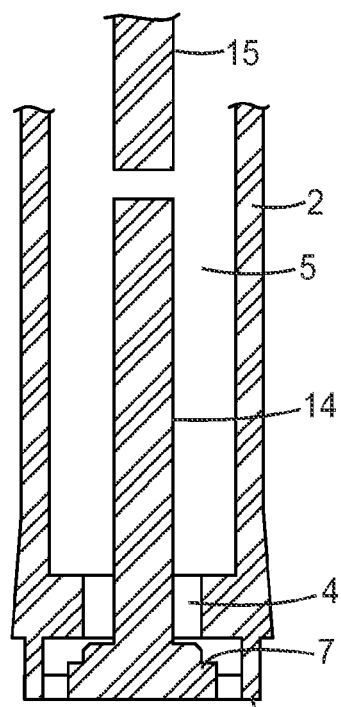
FIG. 7 illustrates a further modification of the piston of FIGS. 1 to 3.

FIG. 7 illustrates a modification of the piston 1 of FIGS. 1 to 3, for use when it may be required to prevent movement of the cap 7 to close the venting passage 4 until certain conditions are established in the storage chamber 10. The piston is modified by the provision of a post 14 on the rear face of the cap 7, which extends through the venting passage 4 and along the passageway 5 in the plunger 2 for a sufficient distance to enable it to be engaged, if required, by a setting tool 15 inserted into the passageway 5 from the rear end of the plunger 2. The setting tool is used to hold the cap 7 in the open position and prevent the cap from moving into the closed position on the plunger 2 even when a force is exerted on the front face of the cap 7 that would normally be sufficient to overcome the action of the spring 8. In this way, it can be ensured that the cap 7 does not close prematurely and is allowed to close only, for example, when it is certain that no air remains in the substance 12 that is to be stored in the chamber 10.

The piston of FIG. 7 is suitable for use in an automated process because it provides a simple way of ensuring that the removal of air from the storage chamber 10 has been completed without the need to detect that the cap 7 has moved into the closed position. To that end, it can be assumed that the automated process will always result in a certain minimum amount of the substance 12 being loaded into the chamber 10 and that the air removal process has been completed once the plunger 2 has been moved into the chamber by a distance sufficient to contact the substance when present in that minimum amount. In the event that a greater amount of the substance 12 has been loaded into the chamber, the excess will simply pass into the passageway 5 in the plunger. In some cases, depending on factors such as the viscosity of the substance 12, it may be possible to achieve a similar result without the use of the setting tool 15 by initially moving the plunger 2 into the chamber 10 at such a slow speed that the cap 7 does not move into the closed position even when the front face of the cap initially encounters the substance. Thereafter, once the plunger 2 has been moved into the chamber by a distance sufficient to contact the substance 12 when present in the minimum amount, the cap 7 can be caused to close by increasing the speed of the plunger.

Figure 8:
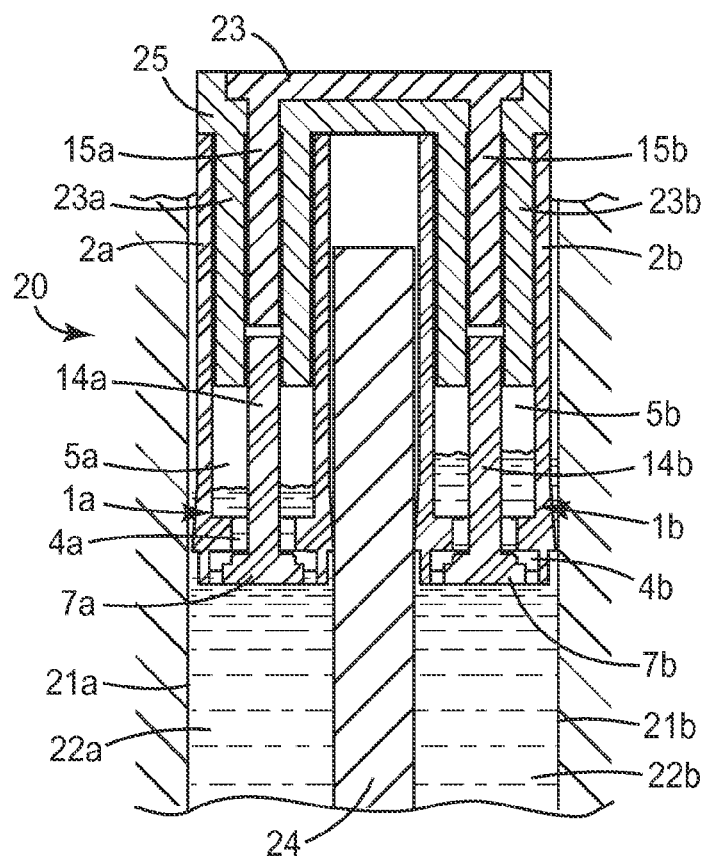
FIG. 8 illustrates two pistons of the type shown in FIG. 7 incorporated in a two-component dispensing cartridge, when the cartridge is being filled.
Figure 9:
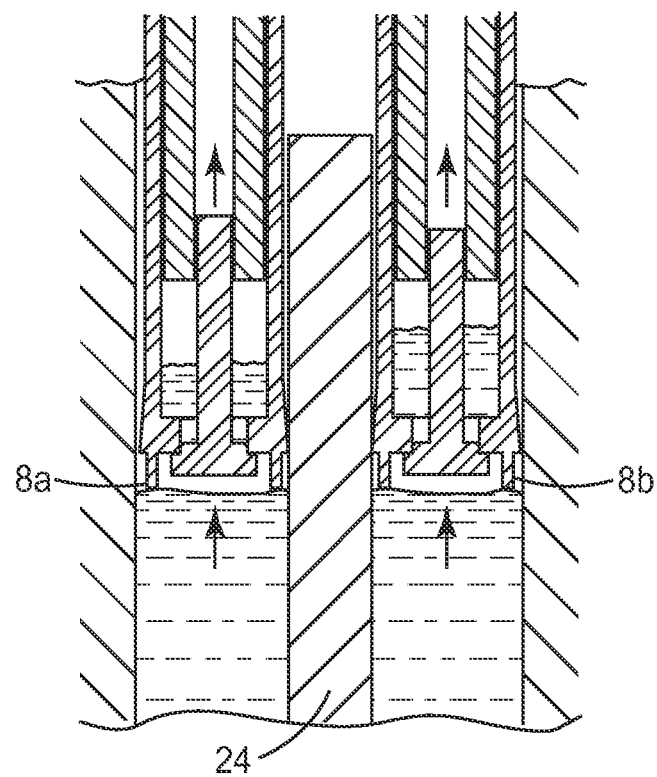
FIG. 9 is similar to FIG. 8 but shows the cartridge after it has been filled.

Pistons of the type shown in FIG. 7 are of particular use in a cartridge having two or more storage chambers in which substances that are to be mixed for use can be stored separately until required. In that situation, it is possible that the substances will not all be filled to the same level in their respective storage chambers, and the pistons can be used to ensure that air will, nevertheless, be removed from all of the storage chambers. This is illustrated in FIG. 8, which shows a diagrammatic cross-section of a cartridge 20 having a first storage chamber 21a for a first substance 22a, and a second storage chamber 21b for a second substance 22b, with a partition 24 between them. FIG. 8 also shows that the plungers 2a, 2b of the respective pistons 1a, 1b in the storage chambers 21a, 21b contain respective sleeves 23a, 23b that surround and guide the respective setting tools 15a, 15b and the ends of the posts 14a, 14b on the rear faces of the respective caps 7a, 7b of the pistons. The setting tools 15a, 15b are coupled together at their rear ends by a connecting bar 23 and are of the same length. The sleeves 23a, 23b are also coupled together at their rear ends by a connector piece 25. In this case, it is assumed that the substance 22b has been filled to a higher level in its storage chamber than the substance 22a. FIG. 8 shows the stage at which the respective pistons 1a, 1b (each of the type shown in FIG. 7) have been pushed, with their respective setting tools 15a, 15b, into the storage chambers 21a, 21b to remove the air from the chambers. Because the storage chamber 21b is filled to a higher level than the chamber 21a, the cap 7b of piston 1b would normally move into the closed position before the cap 7a of piston 1a. This is prevented, however, by the setting tool 15b engaging the post 14b on the rear face of the cap 7b to hold the cap 7b in the open position until both pistons 1a, 1b have moved into the storage chambers 21a, 21b for a sufficient distance to ensure that the air must also have been removed from the chamber 21a. Consequently, after air has been vented from the compartment 21b of the cartridge 20, some of the substance 22b will flow through the venting passage 4b in the piston 1b and into the passageway 5b in the plunger 2b. This will continue until air has been vented from the compartment 21a of the cartridge 20, whereupon the setting tools 15a, 15b are withdrawn, allowing both of the caps 7a, 7b to move into the closed position (shown in FIG. 9) under the action of their respective springs 8a, 8b. The pistons 1a, 1b then remain in the storage position shown in FIG. 9, as described above with reference to FIG. 5, until the cartridge 20 is required for use.

In a cartridge of the type shown in FIG. 8, the pins 14a, 14b of the rear faces of the caps 7a, 7b should be sufficiently long to ensure that, in use, the flowable substance 22a, 22b that is being stored does not pass into the passageway 5a, 5b in the respective plunger 2a, 2b in sufficient quantity to come into contact with the respective locking pin 15a, 15b. Under normal circumstances, however, the hollow plungers 2a, 2b provide adequate space to ensure that this does not occur. The partition 24 between the storage chambers 21a, 21b, as shown in FIG. 8, advantageously does not extend the full length of the cartridge 20 to permit position of the components at the rear end of the cartridge to be adjusted if required.

A cartridge of the type shown in FIG. 8 may comprise more than two storage chambers each provided with a respective piston for discharging a substance from the chamber. Typically, in use, a substance will be stored in each storage chamber of the cartridge.

Figure 10:
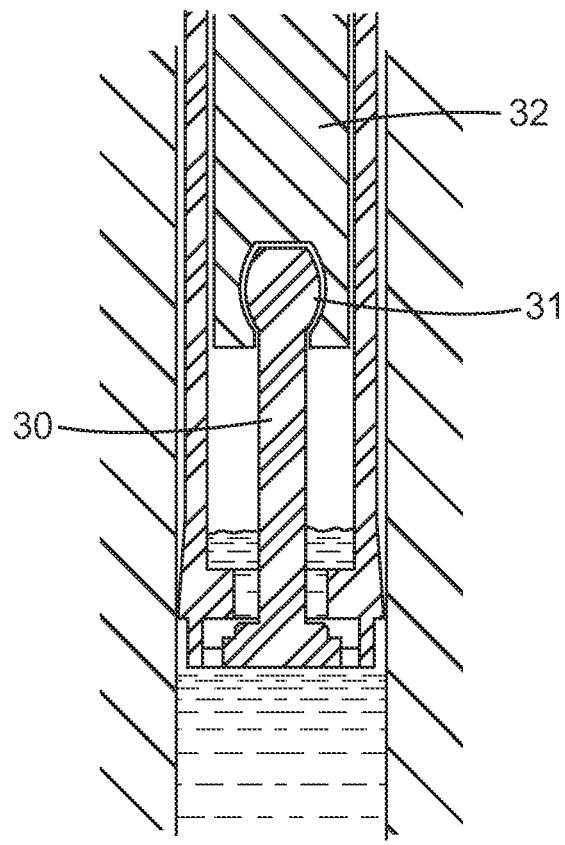
FIG. 10 illustrates a modified form of the piston of FIG. 7 incorporated in a dispensing cartridge, when the cartridge is being filled.
Figure 11:
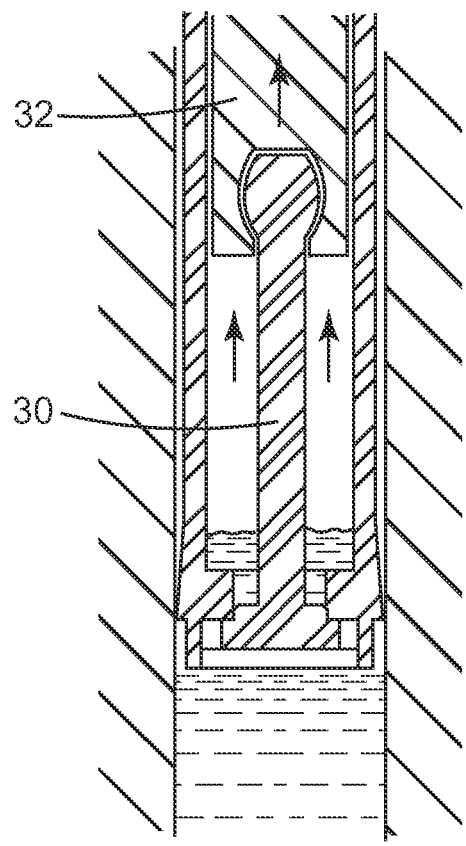
FIGS. 11 and 12 are similar to FIG. 10 but show subsequent stages in the process of filling the cartridge.
Figure 12:
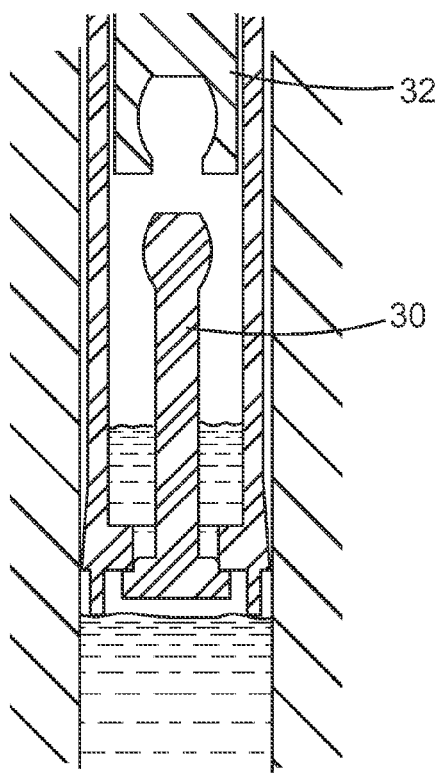

FIGS. 10 to 12 illustrate a modification of the piston of FIGS. 1 to 3, for use when the substance that is being stored in the cartridge does not exert sufficient force on the front face of the cap 7 to move the cap into the closed position against the action of the spring 8. That may happen, for example, if the substance that is being stored in the cartridge is a liquid with a low flow resistance. The piston is again modified by the provision of a post 30 on the rear face of the cap 7, which extends through the venting passage 4 and along the passageway 5 in the plunger 2. In this case, however, the end 31 of the pin is shaped to be retained in the end of a setting tool 32 inserted into the passageway 5 from the rear end of the plunger 2. The setting tool 32 can then be used, if necessary, to pull the cap 7 into the closed position, shown in FIG. 11, once it has been determined (for example, because the plunger 2 has traveled a sufficient distance into the storage chamber as described above) that air has been vented from the storage chamber. The shaping of the end 31 of the pin 30 is such that, when the cap is in the closed position, the setting tool 32 can be disengaged and removed, as shown in FIG. 12. The cap 7 remains in the closed position because it is a press fit in the venting passage 4. If necessary, sealing ribs or similar features can be provided on the cap and/or in the venting passage 4 as described above with reference to FIG. 6 to ensure that the cap remains in the closed position when the setting tool 32 is disengaged.

It will be appreciated that the particular configuration of the spring 8 shown in FIGS. 1 and 2, although advantageous to the manufacture and operation of the piston, could be modified and that other forms of spring could be used to bias the cap 7 into the open position. It will also be appreciated that, although it is advantageous from a cost perspective to manufacture the spring 8, cap 7 and plunger 2 of the piston in one piece by an injection moulding process, alternative manufacturing procedures could be used. For example, the front-end only of the plunger could be moulded in one piece with the cap and the spring, and then attached to the rest of the plunger. Alternatively, all three parts could be formed separately in any suitable way and then attached together.

Figure 14:
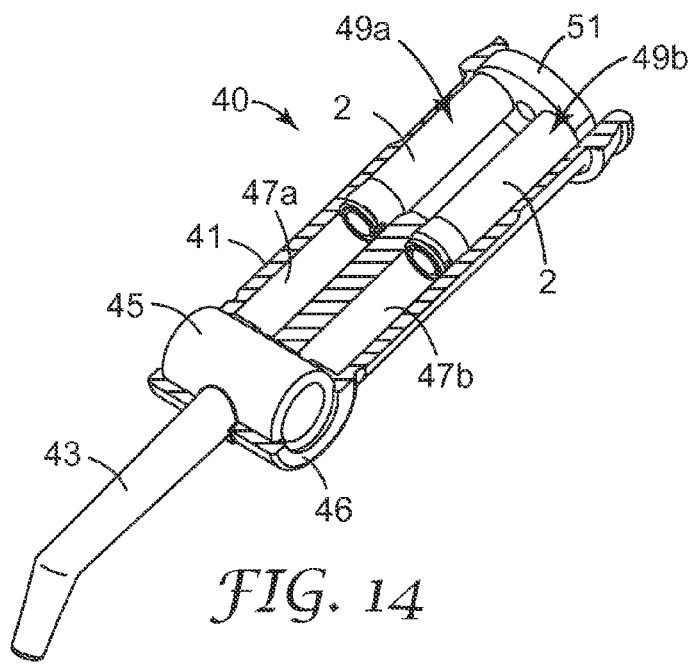
FIGS. 13 and 14 show, respectively, a perspective view and a partial cross-sectional view of a capsule comprising a dispensing cartridge of the type shown in FIGS. 8 and 9.
Figure 13:
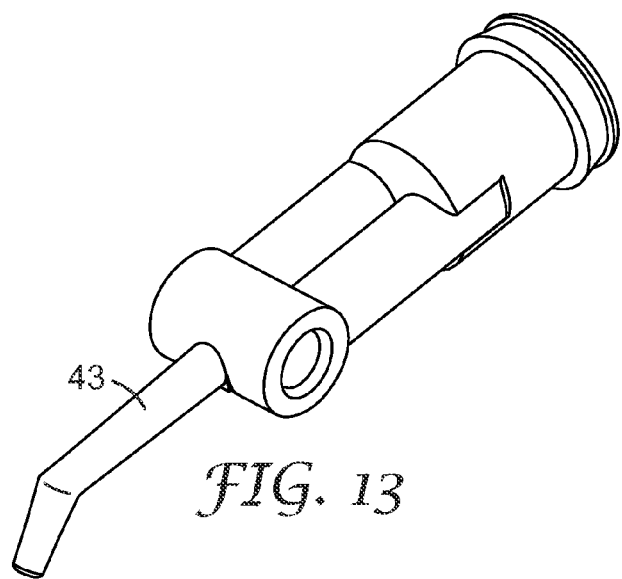

FIGS. 13 and 14 shows a capsule 40 that embodies a two-compartment cartridge 41 of the type illustrated in FIG. 8. The dispensing outlet of the capsule 40 is provided by a cannula 43 extending from a bearing member 45 that is rotatable in a bearing shell 46 at the front end of the capsule. The bearing member 45 is rotatable between a position in which it closes the outlets from storage compartments 47a, 47b within the capsule, and a position (shown in the drawings) in which the outlets from the storage compartments are open and communicate, via the bearing member, with the bore of the cannula. When the bearing member 45 is in the closed position, the cannula 43 extends downwards (as seen in the drawings), substantially at a right angle to the longitudinal axis of the capsule. When the bearing member 45 has been rotated to the open position, shown in the drawings, the cannula 43 is generally aligned with the longitudinal axis of the capsule 40 and can be directed by the dental practitioner to dispense a dental material, comprising a mixture of the substances contained in the storage compartments 47a, 47b, to a selected site within a patient's mouth. The capsule is a single-use item and is then discarded.

A capsule of the general type described above is also described in co-pending PCT application US2007/063635 filed 9 Mar. 2007 in the name of the present applicant.

Each storage compartment 47a, 47b of the capsule 40 contains a respective piston 49a, 49b of the type shown in FIG. 7. As in FIG. 8, the plungers 2 of the pistons are coupled together, at their rear ends, by a connector piece 51 that can be pushed into the capsule 40 to move the pistons 49a, 49b into the storage compartments. As described above, the components (not shown) of the dental material to be dispensed by the capsule 40 are loaded into the storage compartments 47a, 47b from the rear end of the capsule before the pistons 49a, 49b are inserted. The pistons are then used to remove air from the storage compartments 47a, 47b, using setting tools as shown at 15a, 15b in FIG. 8 (described above). During this process, the cannula 43 is in the closed position where it remains until the capsule 40 is required for use. Material is dispensed from the capsule using an appropriately designed hand-held applicator that enables the dental practitioner to exert sufficient pressure on the end cap 51 to push it gradually into the capsule and discharge the contents of the storage compartments 47a, 47b through the cannula 43 (now in the open position), where the materials are mixed by a suitable static mixer before being dispensed to a selected site within a patient's mouth.

An example of an applicator for use with capsules of dental material is described in WO 97/21394.

It will be appreciated that the dental capsule shown in FIGS. 13 and 14 is just one example of how a vented piston in accordance with the invention can be employed. Vented pistons of the type described above with reference to the drawings can find application in many types of dispensing systems in which the material(s) to be dispensed are also required to be stored in the absence of air: examples of such materials include adhesives, sealants and coatings used in industrial and domestic environments; pharmaceutical and medical products; cosmetic products; and food products. The pistons can be used in systems for dispensing single-component materials or materials comprising two or more components that are stored separately and mixed as they are dispensed.

What is claimed is:

1. A vented piston comprising a plunger having a front side and a rear side, a venting passage extending between the front side and the rear side, and a cap on the front side;
    wherein the cap is resiliently-biased towards an open position in which air can pass through the venting passage from the front to the rear side of the plunger,
    wherein the cap is movable from the open position to a closed position in which the cap closes the venting passage,
    wherein the cap is resiliently-biased towards the open position by a spring which is formed as a one-piece moulded component together with the cap and at least a part of the plunger, and wherein the spring comprises a plurality of parts, each of which extends between the cap and the front side of the plunger.

2. A piston as claimed in claim 1, in which the cap, the spring and the plunger are formed as a one-piece moulded component.

3. A piston as claimed in claim 1, in which the spring extends between the cap and the front side of the plunger.

4. A piston as claimed in claim 1, in which the spring extends at least partially around the cap.

5. A vented piston comprising a plunger having a front side and a rear side, a venting passage extending between the front side and the rear side, and a cap on the front side;
   wherein the cap is resiliently-biased towards an open position in which air can pass through the venting passage from the front to the rear side of the plunger,
   wherein the cap is movable from the open position to a closed position in which the cap closes the venting passage,
   wherein the cap is resiliently-biased towards the open position by a spring which is formed as a one-piece moulded component together with the cap and at least a part of the plunger, and
   wherein the spring comprises at least one encircling part which extends at least partially around the cap.

6. A piston as claimed in claim 5, in which the spring comprises a plurality of encircling parts each of which extends around a respective part of the cap and is connected, at one end, to the front side of the plunger and, at the other end, to the cap; and in which the length of each encircling part is substantially greater than the distance travelled by the cap in moving from the open position to the closed position.

7. A piston as claimed in claim 6, in which the spring comprises two encircling parts each of which extends around a respective half, approximately, of the cap and is connected, at one end, to the front side of the plunger and, at the other end, to the cap; wherein the length of each encircling part is substantially greater than the distance traveled by the cap in moving from the open position to the closed position.

8. A piston as claimed in claim 1, in which the cap can be held in the open position by pressure applied thereto from the rear side of the plunger.

9. A piston as claimed in claim 8, in which the cap comprises a post that extends into the venting passage to the rear side of the plunger, whereby the cap can be held in the open position by pressure applied to the post.

10. A piston as claimed in claim 9, in which the post is so shaped that it can be pulled from the rear side of the plunger, to move the cap into the closed position.

11. A piston as claimed in claim 1, comprising sealing means positioned to form a seal between the cap and the plunger when the cap is in the closed position.

12. A piston as claimed in claim 1, in which the plunger is hollow.

13. A dispensing system comprising at least one chamber for storing a substance and, for the/each storage chamber, a respective piston as claimed in claim 1;
   wherein the plunger of the piston is movable into the chamber in the direction of a substance stored therein.

14. A system as claimed in claim 13, in which the/each plunger is movable into the respective storage chamber to discharge a substance from the chamber through a dispensing outlet of the system.

15. A system as claimed in claim 14, comprising a plurality of storage chambers; wherein the dispensing outlet comprises means for mixing the substances from the storage chambers.

16. A method of storing a flowable substance using a system as claimed in claim 13, the method comprising:
   placing the substance in a storage chamber of the system; and
   moving the plunger of the respective piston into the chamber in the direction of the substance, thereby moving the cap of the piston into the closed position.

17. A method as claimed in claim 16, wherein the system used comprises a plurality of storage chambers, the method comprising:
   placing a substance in at least one storage chamber of the system; and
   moving the plunger of the respective piston into the chamber in the direction of the substance, thereby moving the cap of the piston into the closed position.

18. A method of storing a flowable substance using a system as claimed in claim 16, the method comprising:
   placing the substance in a storage chamber of the system while the dispensing outlet is closed; and
   moving the plunger of the respective piston into the chamber in the direction of the substance, thereby moving the cap of the piston into the closed position.

19. A method as claimed in claim 18, including the step of subsequently opening the dispensing outlet, and moving the plunger of the respective piston further into the chamber to discharge the stored substance from the chamber through the dispensing outlet.

* * * * *

UNITED STATES PATENT AND TRADEMARK OFFICE
CERTIFICATE OF CORRECTION

| | |
|---|---|
| PATENT NO. | : 8,453,887 B2 |
| APPLICATION NO. | : 12/594290 |
| DATED | : June 4, 2013 |
| INVENTOR(S) | : Andreas Boehm |

It is certified that error appears in the above-identified patent and that said Letters Patent is hereby corrected as shown below:

In the Claims

Column 10,
Line 10, in Claim 13, delete "the/each" and insert -- the each --, therefor.

Column 10,
Line 13, in Claim 14, delete "the/each" and insert -- the each --, therefor.

Column 10,
Line 36, in Claim 18, delete "16," and insert -- 14, --, therefor.

Signed and Sealed this
Twenty-sixth Day of November, 2013

Margaret A. Focarino
*Commissioner for Patents of the United States Patent and Trademark Office*